United States Patent
Levy

Patent Number: 6,113,581
Date of Patent: Sep. 5, 2000

[54] INFUSION NEEDLE WITH A BIO-DEGRADABLE/ABSORBABLE NEEDLE TIP

[76] Inventor: Orlev Nissenbaum Levy, 12 Ben Tsion Ave., Tel Aviv 63262, Israel

[21] Appl. No.: 09/149,032

[22] Filed: Sep. 8, 1998

[51] Int. Cl.$^7$ ..................................................... A61M 5/32
[52] U.S. Cl. ........................................... 604/272; 604/265
[58] Field of Search ..................................... 604/265, 270, 604/239, 161, 175, 110, 272, 264; 600/575, 577, 582

[56] References Cited

U.S. PATENT DOCUMENTS

| | | |
|---|---|---|
| 4,838,280 | 6/1989 | Haaga . |
| 4,932,963 | 6/1990 | Ritter et al. ............................. 606/224 |
| 4,936,835 | 6/1990 | Haaga ..................................... 604/265 |
| 4,976,704 | 12/1990 | McLees . |
| 5,879,371 | 3/1999 | Gardiner et al. ........................ 604/224 |

*Primary Examiner*—A. T. Nguyen
*Attorney, Agent, or Firm*—Mark M. Friedman

[57] ABSTRACT

An infusion needle for injection, and continuous transport of medicinal fluid into a blood vessel, or body fluid out of organ tissue, for an indefinite extended period of time, such that the infusion needle tip is sufficiently sharp and rigid for puncturing blood vessels and organ tissue, and is made of a bio-degradable and bio-absorbable material, that degrades in and is absorbed by, a patient's body. The presence of the smooth remaining end of the infusion needle, and the absence of the needle tip following bio-degradation, precludes bodily damage and pain caused by movement at the junction of the previously present infusion needle tip and the patient's blood vessel or organ tissue. The infusion needle tip is made of a bio-degradable and bio-absorbable material, consisting of some combination of catgut, polygalactin, polydioxanone, polyglycolic acid, or other similar medically acceptable bio-degradable/absorbable material. This infusion needle is constructed without plastic components, thereby avoiding the disadvantage of plastic in infusion needle construction that involves the potential of the presence of harmful microorganisms, and patient infection.

8 Claims, 3 Drawing Sheets

INFUSION NEEDLE WITH A BIO-DEGRADABLE/ABSORBABLE NEEDLE TIP

FIELD AND BACKGROUND OF THE INVENTION

The present invention relates to medical needles, and more particularly to an infusion needle comprising a bio-degradable and bio-absorbable sterile needle tip. Application of the infusion needle of the present invention for intravenous infusion, involves injection, and continuous delivery of medicinal fluid to a blood vessel, for an extended period of time. Application of the infusion needle of the present invention for extravenous infusion, involves injection, and continuous withdrawal of body fluid from organ tissue, for an extended period of time. To one of ordinary skill in the art, an extended period of time, pertaining to infusion applications (i.e., intra- or extra- venous), is a time span longer than that required (typically, less than several minutes) for injection, and delivery or withdrawal of medicinal or body fluid using a hypodermic needle. An extended period of time in infusion applications refers to a time span of at least several minutes, and can be as long as several weeks, whereby the infusion needle remains in the target blood vessel or organ tissue on a continuous basis.

Current clinical infusion applications, (e.g., intravenous infusion, extravenous infusion (catheterization)) are based on the use of appropriately sharp and sterile metal or metal/plastic medical infusion needles. Two configurations of an infusion needle are in current use. The first infusion needle configuration, applicable to both intravenous and extravenous infusion treatments, is constructed of sterile stainless steel, whereby following injection and penetration of the target blood vessel or organ tissue, the metal infusion needle tip remains in direct contact with the blood vessel or organ tissue, as well as the immediate surrounding area of the blood vessel or organ tissue, during the duration of the infusion treatment. The second infusion needle configuration, which is currently applied in intravenous infusion treatment only (i.e., via hypodermic injection), consists of two components: (i) a metal infusion needle, whereby its function is for initial injection and penetration of a blood vessel, and is withdrawn from the patient immediately (i.e., within a few minutes) following penetration of the blood vessel or organ tissue, leaving behind the second component (ii), a (supposedly sterile) plastic tube which shapely fits around component (i), and which remains in the blood vessel from the tine of withdrawal of component (i) and continues to serve as part of the delivery vehicle for the intravenous medicinal fluid.

Following penetration of a blood vessel or organ tissue, medicinal fluid (e.g., saline solution, blood, plasma, hypotonic-, hypertonic-, and isotonic-liquids, and other liquid medications) or body fluid (e.g., urine), is continuously administered into the blood vessel, or continuously withdrawn from organ tissue, through the remaining metal or plastic hollow cylinder part of an infusion needle. Success in treatment of a patient via infusion depends, among other factors, on the continuity, stability, and sterility of the medicinal or body fluid flow, which itself depends upon the absence of discontinuities, obstructions, or the presence of microorganisms in the upstream fluid supply or reservoir and/or tubing carrying the fluid to or from the infusion needle, located in the blood vessel or the organ tissue. Additionally, important to the success of infusion treatment, is the continuity, stability, and sterility of the fluid flow downstream from the intra- or extra- venous infusion needle, i.e., downstream from the location of the infusion needle, leading to or away from, and including the area surrounding the medicinal or body fluid flowing into or out of, the targeted blood vessel or organ tissue, respectively. Success of an infusion treatment depends strongly upon the status of the junction formed between the infusion needle tip and the blood vessel or organ tissue, and the fluid flow through such a junction.

In clinical infusion treatment applications involving the use of the first described infusion needle configuration (i.e., intra- or extra- venous infusion), an undesirable event, which commonly occurs, is movement of the metal infusion needle, within the blood vessel or organ tissue. Movement of the infusion needle tip is a consequence of normal patient movement. Such movement within the patient (i.e., blood vessel or organ tissue) typically results in some degree of blood vessel or tissue damage and possible hemathomasis (i.e., condition of internal hemorrhage), in addition to considerable pain to the patient. In clinical infusion treatment applications involving the use of the second described infusion needle configuration (i.e., intravenous infusion), it is common for foreign microorganisms to be associated with the plastic tube component which remains inside the blood vessel for the duration of an infusion treatment. Exposure of a blood vessel (and ultimately, a patient's bloodstream) to foreign microorganisms may lead to infection and other complications in a patient, requiring replacement of the infusion needle (in such a case, typically, requiring a change in location of the infusion needle), resulting in significant interuption in the infusion treatment, inconvenience, and possibly unnecessary pain to a patient. Clearly, medical infusion needles in current use have limitations and potential health hazards associated with them, due to the sharpness and potential non-sterility of infusion needle tips.

Currently, no modified needle tip for infusion (intra- or extra- venous) is available which minimizes or eliminates the problems of pain or hemathomasis hazard associated with movement of metal infusion needles or metal infusion needle tips. However, certain modified (e.g., bio-absorbable, self-destructive) medical needle tips have been designed, which are specific to hypodermic syringe or biopsy applications, where there is concern of accidental contamination and/or transmission of healthy patients and health care workers with viruses and diseases, via re-use or accidental use of contaminated hypodermic needles. These inventions attempt to solve the problem of illicit drug users who regularly share needles, which may result in the transmission of viruses and diseases from the bloodstream. However, none of these inventions attempts to prevent internal injury due to infusion needle or needle tip movement during infusion treatment.

For example, U.S. Pat. No. 4,976,704 is based on a hypodermic needle containing a moisture soluble alumnium alloy tip, which, following withdrawal of the needle from the patient, the needle tip automatically dissolves. The patent includes the option in the design of the needle tip, to be dissolvable after single use, or following multiple injections over a period of a few minutes for delivery of local anesthetic at several locations before rendered non-functional. The use of a moisture soluble aluminum alloy in a needle tip for intra- or extra- venous infusion applications, is clearly undesirable, due to the poisonous effect of aluminum in the bloodstream or organ tissue, at the level associated with standard infusion needle tips. No teaching is made for using the described aluminum based needle tip for an infusion application.

Another approach in the modification of medical needle tips, for use in prevention of accidental disease transmission, is taught in U.S. Pat. No. 4,936,835, describing a hypodermic or biopsy needle comprising a bio-absorbable/degradable gelatin cutting/puncturing needle tip. The modified gelatin needle tip disintegrates, thereby rendering the needle useless following single injection. As with the modified needle tip of U.S. Pat. No. 4,976,704, the modified gelatin based needle tip is incapable of application to infusion treatment.

It is apparent that there exists a need for an infusion needle which, concurrent to its principle function of serving as an effective vehicle of medical fluid delivery (or body fluid withdrawal) along with associated requirements of being a medical infusion needle, can be used to prevent, or at least minimize, blood vessel or tissue damage to patients as a result of movement at the junction consisting of the infusion needle tip and the patient's blood vessel or target organ. Additionally, there is a need for such a modified infusion needle whereby there is no potential of microorganism contamination or infection in the patient during infusion treatment, associated with plastic infusion tubes. Moreover, additional and desirable attributes of such an invention of a modified infusion needle include cost effectiveness, and absence of the need for the infusion needle to be part of a mechanism requiring operator manipulation or involvement during the infusion treatment.

SUMMARY OF THE INVENTION

The present invention features a new type of infusion needle, which can be used in intra- and extra- venous infusion applications (i.e., for delivering medicinal fluid, e.g., saline solution, blood, plasma, medications, into a blood vessel, or withdrawal of body fluid, e.g., urine, out of a patient), which fulfills the need of eliminating internal patient injury due to movement of the rigid, sharp infusion needle tip, typically caused by accidental or unavoidable patient movement, and is sterile, thereby removing the potential of microorganism contamination or patient infection.

According to the present invention, there is provided an infusion needle for injection, and continuous transport of intravenous fluids into a blood vessel of a patient for an extended period of time, the infusion needle including: (a) an infusion needle tip including a bio-degradable and bio-absorbable material, the infusion needle tip being sufficiently sharp and rigid for penetration into the blood vessel, and the infusion needle tip being in communication with the blood vessel for fluid delivery into the blood vessel; and (b) a hollow cylinder, for fluid transport, having a first end attached to the infusion needle tip, wherein the first end of the metal hollow cylinder is smooth.

According to the present invention, there is provided an infusion needle for injection, and continuous transport of extravenous fluids out of organ tissue of a patient for an extended period of time, the infusion needle including: (a) an infusion needle tip including a bio-degradable and bio-absorbable material, the infusion needle tip being sufficiently sharp and rigid for penetration into the organ tissue, and the infusion needle tip being in communication with the organ tissue for fluid withdrawal out of the organ tissue; and (b) a hollow cylinder having a first end attached to the infusion needle tip, wherein the first end of the hollow cylinder is smooth.

According to the present invention, there is provided a method for intravenous infusion of fluid into a blood vessel, including the steps of: (a) providing an infusion needle, the infusion needle featuring an infusion needle tip including a bio-degradable and bio-absorbable material, the infusion needle tip being sufficiently sharp and rigid for penetration into the blood vessel, and the infusion needle tip being in communication with the blood vessel for fluid delivery into the blood vessel; (b) inserting the infusion needle tip into the blood vessel; and (c) allowing biodegradation of the infusion needle tip, such that the infusion needle tip is degraded; and (d) infusing fluid through the infusion needle.

According to the present invention, there is provided a method for extravenous infusion of fluid out of organ tissue, including the steps of: (a) providing an infusion needle, the infusion needle featuring an infusion needle tip including a bio-degradable and bio-absorbable material, the infusion needle tip being sufficiently sharp and rigid for penetration into the organ tissue, and the infusion needle tip being in communication with the organ tissue for fluid withdrawal out of the organ tissue; (b) inserting the infusion needle tip into the organ tissue; and (c) allowing biodegradation of the infusion needle tip, such that the infusion needle tip is degraded; and (d) infusing fluid through the infusion needle.

The infusion needle of the present invention is to be used in intravenous and extravenous infusion applications, replacing current, standard metal and metal/plastic infusion needles. Rendering of the infusion needle of the present invention harmless to a blood vessel or organ tissue, and ultimately to a patient undergoing infusion treatment, is based on the ability of the infusion needle tip to bio-degrade and be bio-absorbed in a patient's body, during the infusion treatment, without need for additional chemical or medicinal treatment of the internal bodily junction including a blood vessel (or organ tissue) and the infusion needle tip, in addition to the sterility of the part of the infusion needle remaining in a blood vessel or organ tissue. Following biodegradation of the infusion needle tip, the remaining smooth end of the standard metal hollow cylinder previously attached to the infusion needle tip, maintains contact with either a blood vessel or organ tissue, is sterile, and enables uninterrupted continuation of fluid delivery or fluid withdrawal. As a consequence of the smooth, sterile end of the remaining infusion needle, ordinary movement of the infusion needle during infusion treatment is expected to have no harmful affect on the patient.

BRIEF DESCRIPTION OF THE DRAWINGS

Reference is now made to the drawings which illustrate the preferred embodiment the invention may take in physical form and in certain parts and arrangements of parts wherein.

DESCRIPTION OF THE PREFERRED EMBODIMENTS

The components and operation of an infusion needle with a bio-absorbable/degradable tip according to the present invention are better understood with reference to the drawings and the accompanying description. It is to be noted that illustrations of the present invention shown here are for illustrative purposes only and are not meant to be limiting. For the purpose of preciseness, yet completeness, the following embodiment of the present invention describes an infusion needle and an infusion needle tip to be used in intravenous infuision applications; words or terms required to properly describe the infusion needle and infusion needle tip of the present invention and their applicability to extra-venous infusion are parenthesized.

Figure 1:
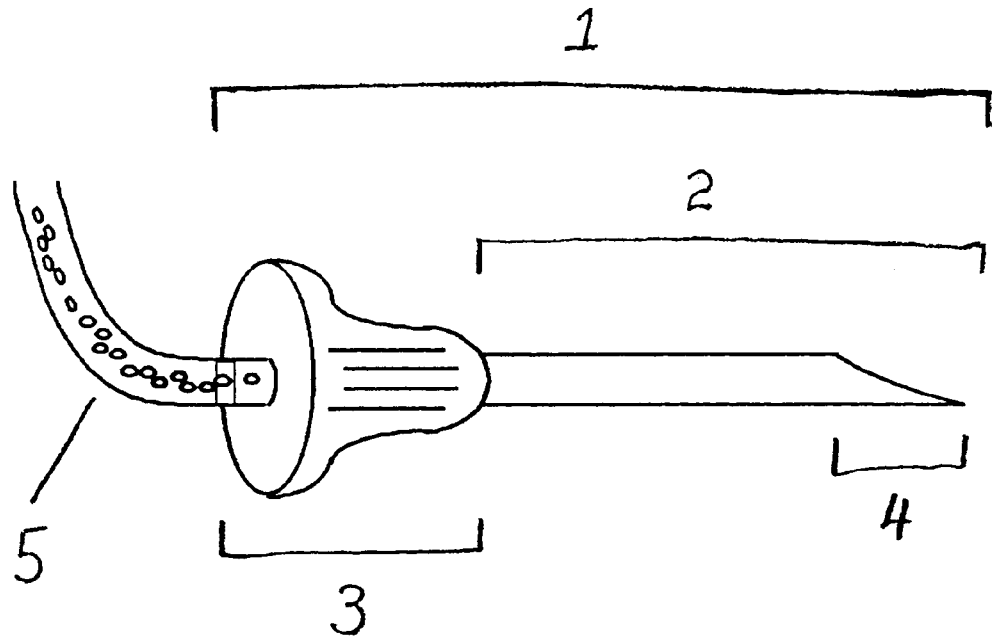
FIG. 1 is an illustration one configuration of a typical infusion needle currently in use.

Referring now to the drawings, FIG. 1 illustrates a typical conventional infusion needle in current clinical use. The infusion needle 1, includes the exposed portion of the metal hollow cylinder 2, protruding from a plastic syringe connector 3; and the distal end of the metal hollow cylinder 2, considered the needle tip 4, functioning as the cutting element of the infusion needle. In intravenous (extravenous) infusion applications, medicinal (body) fluids are supplied to (withdrawn from) the infusion needle through a medical grade fluid delivery (withdrawal) tube 5. The metal hollow cylinder 2, has typical dimensions of 40–65 mm in length and a diameter, of the non-tip portion, of 1–1.4 mm. The plastic syringe connector 3, providing connection of the medicinal (body) fluid supply tube 5 to the metal hollow cylinder 2, is typically 8–12 mm in length. The infusion needle tip 4, comprising the rigid, sharp, tapered, distal end portion of the metal hollow cylinder, is about 5 mm in length.

Initiation of infusion treatment involves penetration of a blood vessel (i.e., intravenous) or organ tissue (i.e., extravenous) via the infusion needle tip 4. For effective infulsion treatment, including efficient fluid delivery to a target blood vessel, or fluid withdrawal from target organ tissue, respectively, the entire needle tip 4 is subcutaneously located in the patient. Remaining external to the patient during the infusion treatment include: part of the protruding portion of t he metal hollow cylinder 2, the syringe connector 3 (containing the non-protruding portion of the metal hollow cylinder (not shown), and the fluid delivery (withdrawal) tube 5. Clearly, following penetration of the needle tip 4, along with subcutaneous location of part of the metal hollow cylinder 2, direct movement or motion of, the infusion needle components 2, 3, or 5, or direct movement or motion of, the patient in the vicinity of the infusion needle components 2, 3, or 5, will translate to movement at the in tern al junction consisting of the blood vessel (tissue area) and the infusion needle tip 4. This, in turn, will likely result in internal damage to at least the blood vessel (organ tissue) containing the infusion needle tip 4, which consequently leads to pain, discomfort, and potentially hemathomasis in the recipient of the infusion treatment.

Figure 2:
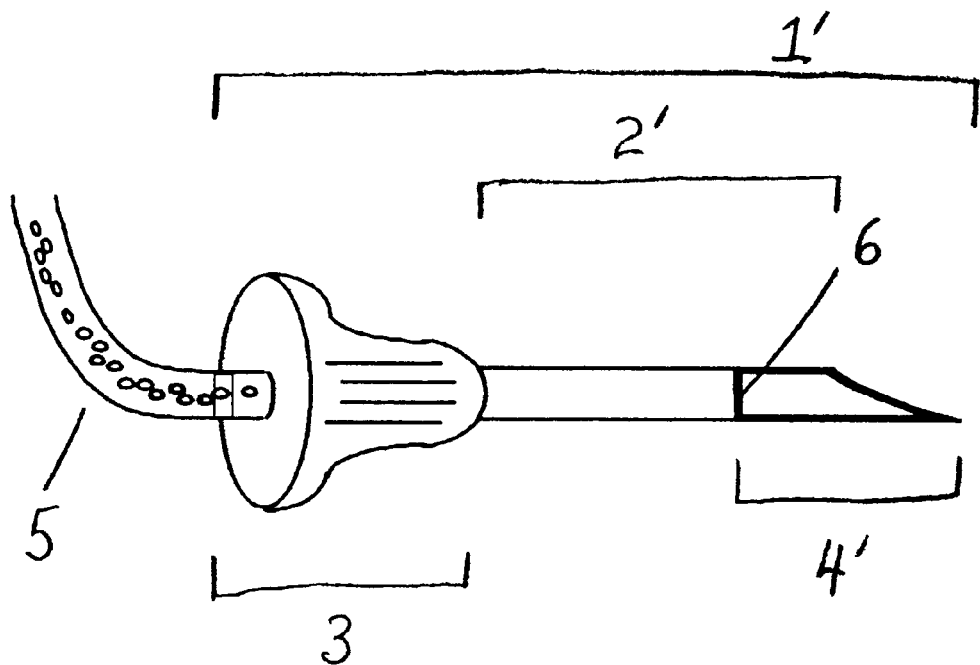
FIG. 2 is an illustration of the infusion needle of the present invention, showing the tip comprised of a bio-absorbable/degradable material, and approximate dimensions of the infusion needle and infusion needle tip.

FIG. 2 illustrates the preferred embodiment of the infusion needle 1', of the present invention, showing the position of the proposed bio-degradable/absorbable needle tip 4', replacing the needle tip 4 of the conventional infusion needle (FIG. 1) in current use, and its relation to the location of the protruding portion of the metal hollow cylinder 2', the plastic syringe connector 3, and the medicinal (body) fluid delivery (withdrawal) tube 5. The infusion needle tip 4' of the present invention is about 4–7 mm in length, with the diameter of the non-tapered, dull end, adjacent and connecting to the protruding portion of the metal hollow cylinder 2', is the same as that of the metal hollow cylinder, i.e., typically 1–1.4 mm.

The infusion needle tip 4' of the present invention is comprised of a bio-absorbable and bio-degradable material, of acceptable clinical medical use. The bio-degradable/absorbable needle tip is preferably constructed of catgut. Catgut is well known as a primary material currently used for suturing in surgical procedures, having a relatively short half-life in the body (e.g., 'Comparison Of The Degree Of Abdominal Adhesion Formation Associated With Chromic Catgut And Polypropylene Suture Materials', Rochat, M. C., et. al., American Journal of Veterinary Research, 1996, Jun, 57 (6): 943–947; 'Ligation Of The Structures Of The Cystic Pedicle During Laparoscopic Cholecystectomy', Nathanson, L. K., et. al., American Journal of Surgery, 1991, Mar, 161 (3): 350–354; and 'Evaluation Of The Effectiveness Of The Use Of Various Anti-adhesion Agents In An Experiment', Adamian, L. V., et. al., Biull Eksp Biol Med, 1993, Jan, 115 (1): 68–69).

Alternatively, and preferably, the infusion needle tip is constructed from some other chemical, for instance, an organic polymer, such as polygalactin, polydioxanone, or polyglycolic acid, each having proven and effective bio-degradable and bio-absorbable properties in the body, during clinical applications (e.g., 'Comparison Of Seven Different Suture Materials In The Feline Oral Cavity', DeNardo G. A., et. al., Journal of the American Animal Hospital Association, 1996 March; 32 (2): 164–172.). Alternatively, and preferably, the infusion needle tip is constructed of a combination of catgut and another appropriate medically acceptable material.

The end of the protruding metal hollow cylinder 2' facing in the opposite direction of the medicinal fluid delivery tube input to the plastic syringe connector 3, and which is one part of the interface, 6, formed between the protruding metal hollow cylinder 2' and the non-sharp end of the infusion needle tip 4', is designed to be smooth and harmless during interaction with blood vessels and body tissue. The actual relative lengths of the protruding portion of the metal hollow cylinder 2' and design characteristics of the infusion needle tip 4' (e.g., degree of rigidity, sharpness, length, wall thickness) can vary according to the criteria of the actual infusion application (i.e., intra- or extra- venous, for example), including required depth of subcutaneous infusion needle penetration.

Figure 3:
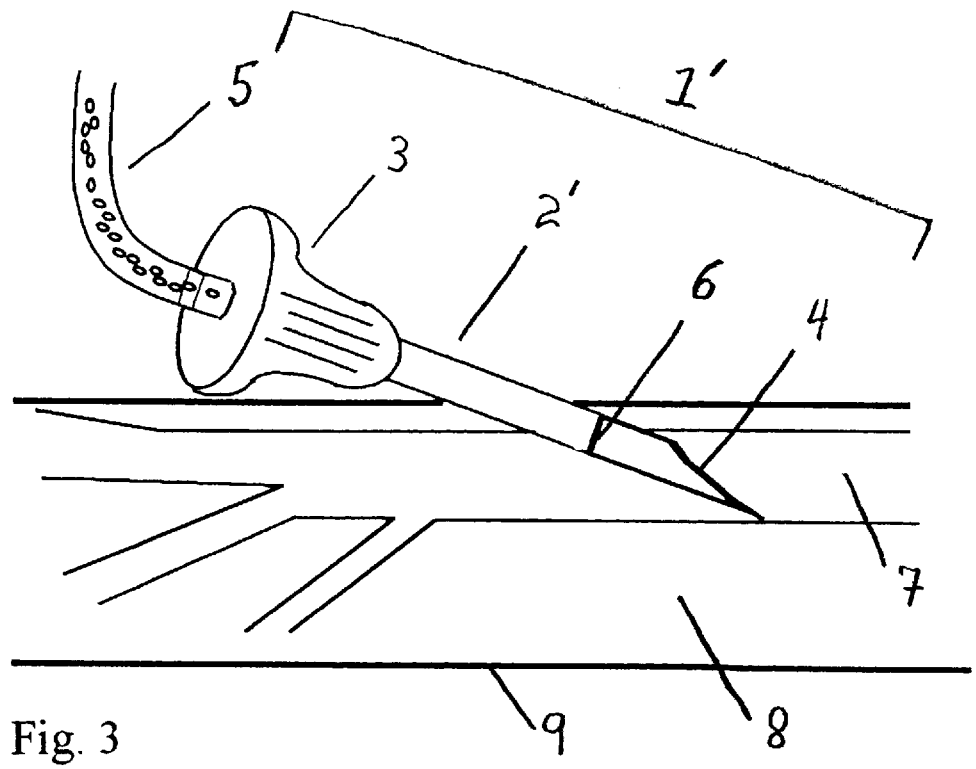
FIG. 3 is an illustration of the infusion needle of FIG. 2, shortly following intravenous injection and penetration into a blood vessel of a patient, prior to bio-absorption/degradation of the infusion needle tip.

FIG. 3 is an illustration of the infusion needle 1', of the present invention, shortly following intravenous injection via penetration of the patient's skin 9, surrounding body tissue 8, and target blood vessel 7, prior to bio-absorption/degradation of the needle tip 4'. In the case of injection of an extravenous infusion needle (not shown here), the infusion needle tip 4' would penetrate the patient's skin 9, and be lodged in the tissue area 8. As for the conventional infusion needle 1 (FIG. 1), injection and penetration also occurs via the sharp, rigid, infusion needle tip 4', while it is attached to the protruding portion of the metal hollow cylinder 2'. During, and at least for a minimum time period, immediately following injection and penetration of the proposed needle tip 4' into the blood vessel 7, the configuration of the proposed needle tip 4', including the needle tip interface 6 (formed between the protruding metal hollow cylinder 2' and the non-sharp end of the proposed needle tip 4'), is maintained similar to that of the conventional needle tip 4 of the conventional infusion needle 1. Key to the maintenance of the initial configuration of the infusion needle tip 4', (i.e., in order to assure effective and painless injection and penetration of the infusion needle tip into the patient) are the sharpness and rigidity characteristics, which in turn are dependent upon the material used in the manufacture of the bio-degradable/absorbable infusion needle tip 4'. The infusion needle tip 4' of the present invention, undergoes bio-degradation, thereby precluding its initial sharpness and rigidity from causing damage to the blood vessel 7, and possibly, to the patient's tissue area 8 surrounding the blood vessel 7, as is the circumstance with the conventional infusion needle tip 4 (FIG. 1).

Figure 4:
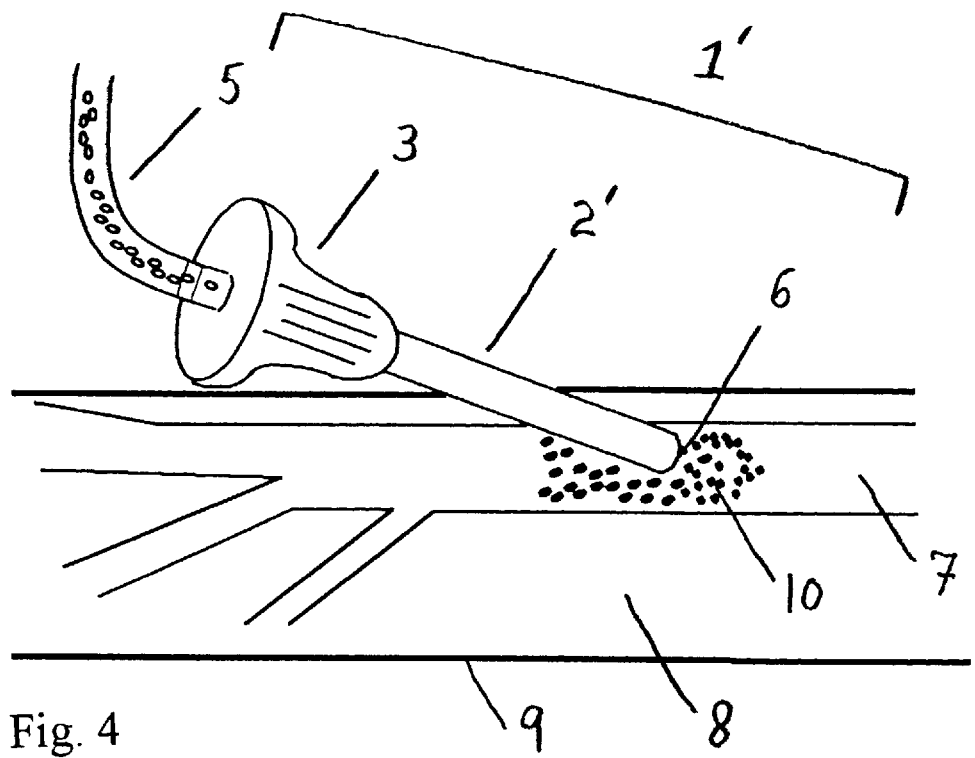
FIG. 4 is an illustration of the infusion needle of FIG. 2, showing the infusion needle tip undergoing bio-degradation and bio-absorption inside a blood vessel.

FIG. 4 is an illustration of the infusion needle 1', of the present invention, showing the proposed needle tip 4' undergoing bio-degradation and bio-absorption inside the blood vessel 7, resulting in the remains 9 of the infusion needle tip material. Immediately apparent is the absence of the infusion needle tip 4' (of FIGS. 2 and 3) in its original structure (i.e., form, rigidity, sharpness). The smooth, harmless infusion needle tip interface 6, instead of the rigid, sharp needle tip, is now exposed to the blood vessel 7 (in extravenous infusion applications, the smooth, harmless infusion needle tip interface 6 is exposed to the tissue area 8). At this stage of the intravenous infusion treatment with the infusion needle 1', there is no longer the possibility of damage to the blood vessel 7, or to surrounding tissue 8, by the rigid, sharp infusion needle tip 4'. In the case of extravenous infusion, the absence of the rigid, sharp infusion needle tip 4', and the presence of the smooth, infusion needle tip interface 6, precludes the possibility of penetration into the blood vessel 7, or damage to surrounding tissue 8.

Figure 5:
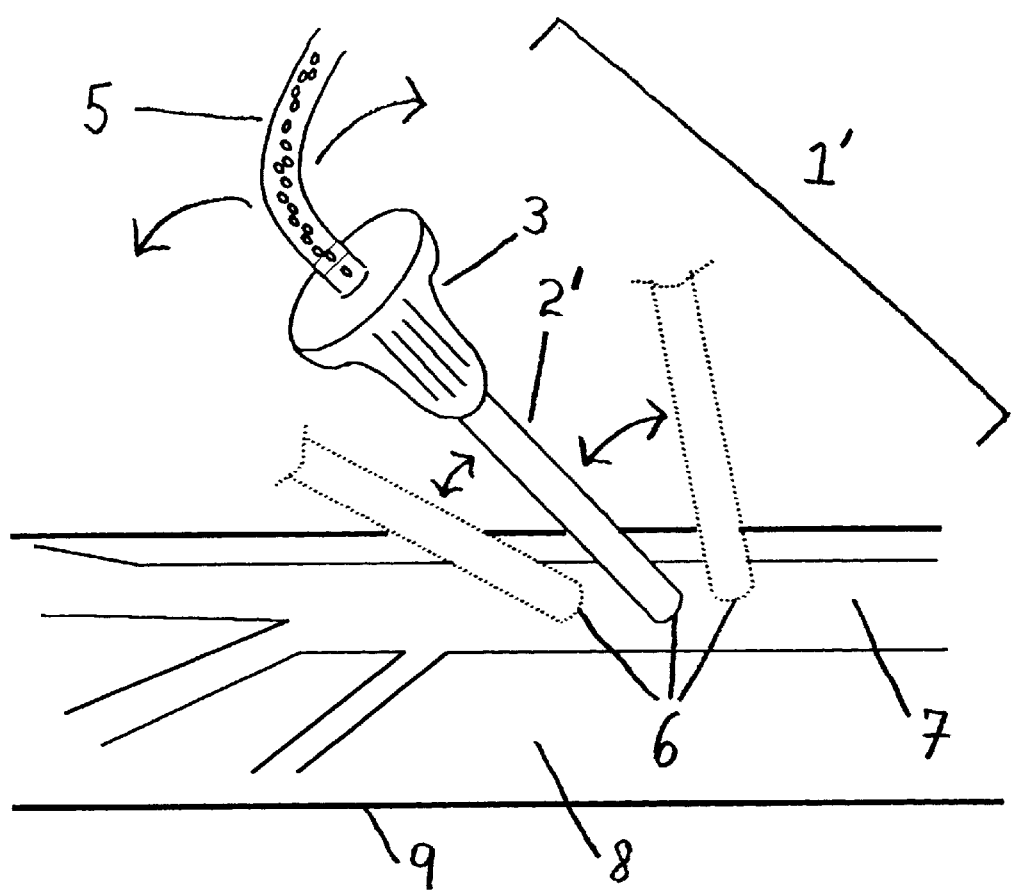
FIG. 5 is an illustration of the infusion needle following bio-degradation and bio-absorption of the infusion needle tip, indicating elimination of internal bodily injury and bodily pain due to movement of the initially sharp, rigid infusion needle tip, and the absence of harmful infusion needle tip material.

FIG. 5 is an illustration of the infusion needle 1', of the present invention, following completion of bio-degradation and bio-absorption of the proposed infusion needle tip 4' (initially shown in FIGS. 2 and 3), showing the absence of the remains 9 of the bio-degradable/absorbable material of the infusion needle tip 4'. FIG. 5 is indicative of the elimination of the potential for internal bodily injury and bodily pain due to infusion needle tip movement at the junction formed between the infusion needle tip interface 6 (i.e., the remaining protruding portion of the metal hollow cylinder 2' of the infusion needle) and the blood vessel 7, or surrounding tissue area 8. Moreover, this figure illustrates how after incidental patient movement, or movement of the remaining infusion needle components, including the remaining protruding portion of the metal hollow cylinder 2', the plastic syringe connector 3, or the medicinal fluid delivery (withdrawal) tube 5, no longer constitutes a problem; the absence of the bio-degradable/absorbable infusion needle tip 4', and the presence of the now exposed smooth needle tip interface 6, precludes health hazard associated with further infusion needle tip penetration into the blood vessel 7 or surrounding tissue area 8, in addition to elimination of the potential of hematomasis, and associated bodily pain.

While the invention has been described with respect to one embodiment, it will be appreciated that many variations, modifications and other applications of the invention may be made.

What is claimed is:

1. An infusion needle for injection and continuous transport of intravenous fluids into a blood vessel of a patient for an extended period of time, said infusion needle comprising:

(a) an infusion needle tip comprised of a bio-degradable and bio-absorbable material, said material is selected from the group consisting of catgut, polygalactin polydioxanone, and polyglycolic acid, said needle tip being sufficiently sharp and rigid for penetration into the blood vessel; and (b) a metal hollow cylinder having a first end attached to said infusion needle tip, wherein said first end of said metal hollow cylinder is smooth.

2. The infusion needle of claim 1, further comprising:

(c) a fluid delivery tube in fluid communication with a second end of said hollow cylinder.

3. The infusion needle of claim 2, further comprising:

(d) an infusion needle syringe connector coupled between said hollow cylinder and said fluid delivery tube.

4. An infusion needle for injection and continuous transport of extravenous fluids out of organ tissue of a patient for an extended period of time, said infusion needle comprising:

(a) an infusion needle tip comprised of a bio-degradable and bio-absorbable material, said material is selected from the group consisting of catgut, polygalactin, polydioxanone, and polyglycolic acid, said needle tip being sufficiently sharp and rigid for penetration into organ tissue; and (b) a metal hollow cylinder having a first end attached to said infusion needle tip, wherein said first end of said metal hollow cylinder is smooth.

5. The infusion needle of claim 4, further comprising:

(c) a fluid withdrawal tube in fluid communication with a second end of said hollow cylinder.

6. The infusion needle of claim 5, further comprising:

(d) an infusion needle syringe connector coupled between said hollow cylinder and said fluid withdrawal tube.

7. A method for intravenous infusion of fluid into a blood vessel, comprising the steps of:

(a) providing an infusion needle, said infusion needle featuring an infusion needle tip comprised of a bio-degradable and bio-absorbable material, said material is selected from the group consisting of catgut, polygalactin, polydioxanone, and polyglycolic acid, said needle tip being sufficiently sharp and rigid for penetration into the blood vessel;

(b) inserting said infusion needle tip into the blood vessel;

(c) allowing biodegradation of said infusion needle tip, such that said infusion needle tip is degraded; and (d) infusing fluid through said infusion needle.

8. A method for extravenous infusion of fluid out of organ tissue, comprising the steps of:

(a) providing an infusion needle, said infusion needle featuring an infusion needle tip comprised of a bio-degradable and bio-absorbable material, said material is selected from the group consisting of catgut, polygalactin, polydioxanone, and polyglycolic acid, said needle tip being sufficiently sharp and rigid for penetration into the organ tissue;

(b) inserting said infusion needle tip into the organ tissue;

(c) allowing biodegradation of said infusion needle tip, such that said infusion needle tip is degraded; and (d) infusing fluid through said infusion needle.

* * * * *